(12) United States Patent
Workman

(10) Patent No.: US 6,832,524 B2
(45) Date of Patent: Dec. 21, 2004

(54) GROUT SAMPLE UNBONDED CAPPING SYSTEM

(75) Inventor: Gary Workman, Bellwood, IL (US)

(73) Assignee: Deslauriers, Inc., Bellwood, IL (US)

( * ) Notice: Subject to any disclaimer, the term of this patent is extended or adjusted under 35 U.S.C. 154(b) by 3 days.

(21) Appl. No.: 10/235,159

(22) Filed: Sep. 5, 2002

(65) Prior Publication Data

US 2004/0045366 A1 Mar. 11, 2004

(51) Int. Cl.[7] ............................ G01N 3/00; G01N 11/00
(52) U.S. Cl. .......................................... 73/803; 73/788
(58) Field of Search .................... 73/803, 788, 853, 73/818, 825, 857

(56) References Cited

U.S. PATENT DOCUMENTS

| 2,414,550 A | * | 1/1947 | Patch et al. ................... 73/825 |
| 3,545,263 A | * | 12/1970 | Hadley et al. ................. 73/825 |
| 4,445,387 A | * | 5/1984 | Hall et al. .................... 73/845 |
| 4,740,025 A | * | 4/1988 | Nelson ....................... 294/99.1 |
| 6,591,691 B2 | * | 7/2003 | Kim et al. ..................... 73/803 |

OTHER PUBLICATIONS

"Concrete Testing Products for the Construction Industry", Product Guide, Deslauriers, Inc., Apr., 2000.

* cited by examiner

Primary Examiner—Edward Lefkowitz
Assistant Examiner—Lilybett Martir
(74) Attorney, Agent, or Firm—Wood, Phillips, Katz, Clark & Mortimer

(57) ABSTRACT

An unbonded capping system is provided for compression testing of grout samples in the form of rectangular prisms. The capping system comprises first and second retaining cups comprising metal blocks each having opposite parallel planar surfaces. A first of the planar surfaces is engagable by a test platen, in use. A second of the planar surfaces has a rectangular cavity for receiving one end of the grout sample. First and second rectangular compression pads each have a hardness in the range of about 50–70 durometer. The compression pads are of a size slightly smaller than a size of the rectangular cavities to be received therein to distribute a test load from the test platens to the grout sample.

20 Claims, 2 Drawing Sheets

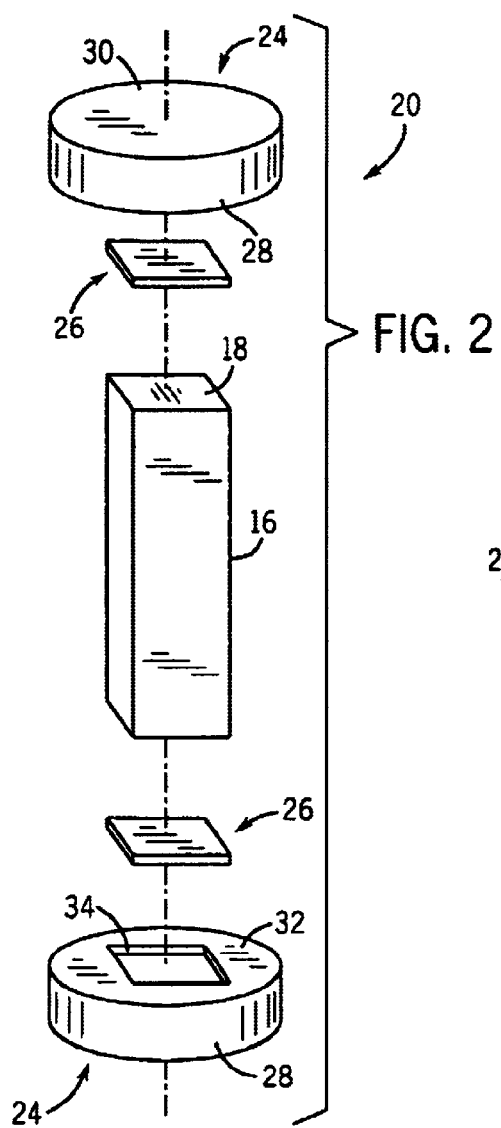
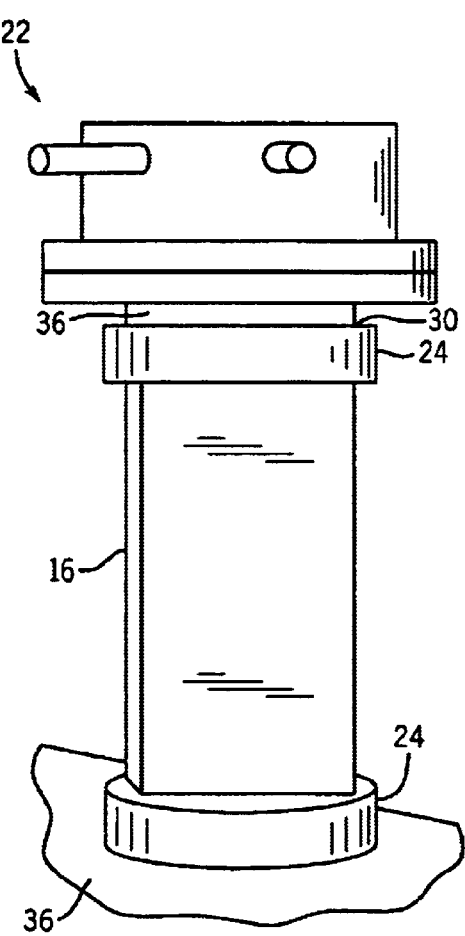
FIG. 2
FIG. 3

US 6,832,524 B2

GROUT SAMPLE UNBONDED CAPPING SYSTEM

FILED OF THE INVENTION

This invention relates to compression testing of grout samples and, more particularly, to an unbonded capping system.

BACKGROUND OF THE INVENTION

Grout is a material used in reinforced masonry construction. Particularly, grout is placed in the cells of hollow concrete masonry units, sometimes referred to as cinder blocks. The grout must be fluid so that it completely fills the cells to provide a solid, grouted masonry wall. To satisfy these requirements, the grout is more fluid than concrete or mortar. Particularly, concrete typically has a slump in the range of 2 inches to 6 inches. Mortar typically has a slump in the range of 5 inches to 8 inches. Grout typically has a slump in the range of 8 inches to 10 inches. This fluidity allows the grout to flow through the grout space, around reinforcing bars and completely surround and bond to steel and concrete masonry units.

Presently, grout samples are tested for compression as a verification of strength. The traditional method for forming three grout samples for testing is to configure twelve concrete masonry units to form three chambers in the form of rectangular prisms. The chambers are lined with filter paper or other paper product. The chambers are filled with grout which is allowed to harden. An alternative procedure for forming grout samples is a grout sample box 10, see FIG. 1, made of corrugated cardboard. The grout sample box includes a divider 12 that divides the box into four rectangular compartments 14. Each compartment 14 is filled with grout which then hardens to form samples 16 in the form of rectangular prisms. Particularly, each sample has generally square-shaped end walls 18. As is apparent, the particular size of the overall sample and each wall is dependent on the apparatus used for forming the grout sample.

Compression tests of the grout samples are performed by placing the sample between platens of a testing apparatus and the sample compressed until it fails. The platens are planar. Imperfections in the end walls can create pressure points that distort the compression tests. Current procedures require the grout samples to be capped with a sulfur compound to provide a smooth, hard surface which fills any imperfections which normally occur when making grout samples. Capping the grout sample using sulfur compound requires the sulfur to be heated, poured into a capping fixture, placed onto the grout sample and allowed to cool. This procedure requires considerable preparation time. Additionally, the heating of the sulfur compound not only gives off noxious odors but the vapors may combine with humidity in the air to create sulfuric acid. This acid is airborne and over time damages equipment and structures and, more importantly, can create a health hazard.

The present invention is directed to further improvements in grout sample compression testing.

SUMMARY OF THE INVENTION

In accordance with the invention, there is provided an unbonded capping system for compression testing of grout samples.

Broadly, in accordance with one aspect of the invention an unbonded capping system is provided for compression testing of grout samples in the form of rectangular prisms. The capping system comprises first and second retaining cups comprising metal blocks each having opposite parallel planar surfaces. A first of the planar surfaces is engagable by a test platen, in use. A second of the planar surfaces has a rectangular cavity for receiving one end of the grout sample. First and second rectangular compression pads each have a hardness in the range of about 50–70 durometer. The compression pads are of a size slightly smaller than a size of the rectangular cavities to be received therein to distribute a test load from the test platens to the grout sample.

In accordance with another aspect of the invention, the unbonded capping system comprises first and second rectangular elastomeric compression pads.

It is a feature of the invention that the compression pads may each have a hardness of about 50 durometer.

It is another feature of the invention that the first and second retaining cups may be of high alloy steel construction.

It is a further feature of the invention that the first and second retaining cups may be cylindrically shaped and the parallel planar surfaces define end walls.

It is yet another feature of the invention that the first and second rectangular compression pads may comprise neoprene pads.

It is yet a further feature of the invention that the rectangular cavities may comprise square cavities.

It is still a further feature of the invention that the rectangular cavity size may be larger than the size of an end face of the grout sample.

Further features and advantages of the invention will be readily apparent from the specification and from the drawings.

BRIEF DESCRIPTION OF THE DRAWINGS

FIG. 2 is an exploded view of an unbonded capping system in accordance with the invention for compression testing of a grout sample in the form of a rectangular prism; and FIG. 3 is a perspective view of a test apparatus utilizing the unbonded capping system of FIG. 2.

DETAILED DESCRIPTION OF THE INVENTION

Figure 1:
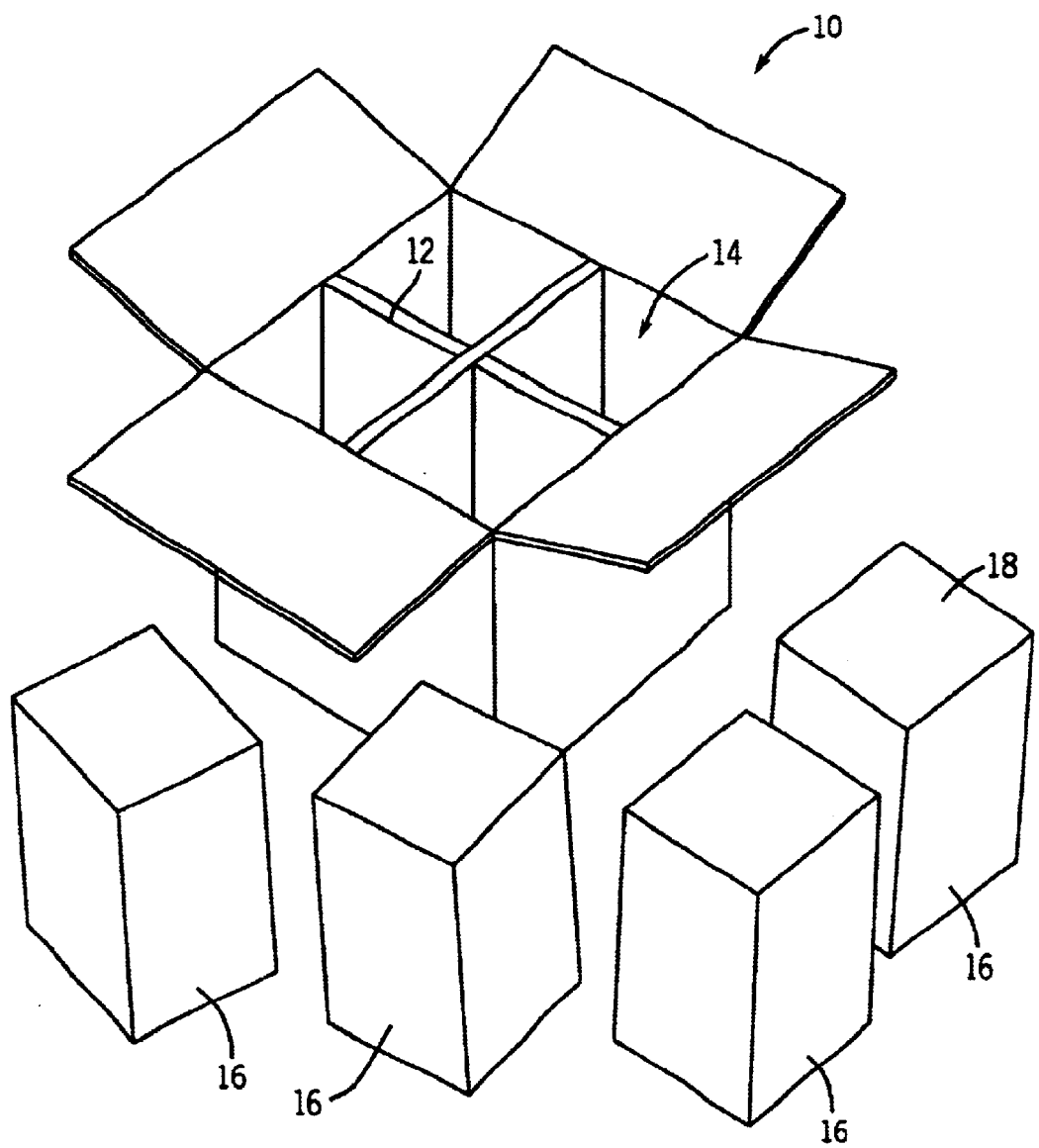
FIG. 1 is a perspective view of a grout sample box used to produce grout samples in the form of rectangular prisms.

In accordance with the invention, there is provided an unbonded capping system 20, see FIG. 2, for compression testing of a grout sample 16 in the form of a rectangular prism. The unbonded capping system is adapted to be used with a compression testing apparatus 22, see FIG. 3.

The grout sample 16 can be formed as discussed previously relative to FIG. 1 or using other well known techniques. Conventionally, the end wall 18 of the grout sample 16 is approximately a 4 inch by 4 inch square. The height of the grout sample 16 is approximately twelve inches. As is apparent, depending on the procedure used for forming the grout sample, the exact dimensions may vary.

The unbonded capping system 20 comprises first and second retaining cups 24 and first and second compression pads 26. Each of the retaining cups 24 is identical in construction. Similarly, each compression paid 26 is identical in construction.

Each retaining cup 24 comprises a metal cylindrical block 28 having opposite parallel planar surfaces 30 and 32 defining end walls. The second planar surface 32 includes a rectangular cavity 34. In the illustrated embodiment to the invention, the cavity 34 is square shaped.

Each retaining cup 24 may be machined from high alloy steel to the same tolerance as platens 36 of the testing apparatus 22, see FIG. 3. The high alloy steel has minimal temperature variation and no deflection under loads. The high strength alloy steel retaining cups 24 resist scratching, thus eliminating the need for additional machining. In the illustrated embodiment of the invention, each retaining cup 24 has a diameter of about 7 inches and a height of about 1½ inches. The cavity 34 is about 3.685 inches square with a depth of about 1 inch. Particularly, the cavity 34 is adapted to be larger in proportion than the desired size of the grout sample end walls 18, which are seldom true in dimension and in squareness. However, the cavity 34 cannot be too large which could result in over hang of the compression pads 26 at sides of the grout sample 16.

The compression pads 26 are rectangular in shape and are made of a tough elastomeric material. The elastic material may be, for example, neoprene. The purpose of the compression pads 26 is to fill in any imperfections which occur during casting of the grout sample 16. Since grout is softer than concrete, the compression pads 26 must be formed of a softer material than would be used with compression pads for concrete samples. Advantageously, the compression pads 26 have a hardness in the range of about 50 to 70 durometer and in one embodiment are formed of 50 durometer neoprene. Such compression pads 26 are adapted to fill imperfections in the grout sample 16. If the compression pad 26 was excessively hard, then point pressure would occur on the imperfections of the grout sample 16 and result in poor test data.

Each compression pad 26 is of a size slightly smaller than the rectangular cavities 34 to be received therein. In the exemplary retaining cups 24 discussed above, the compression pads 26 may have dimensions of 3.625 inches square and depth of ½ inch.

As is apparent, the dimensions described above are intended for use with the standard size grout sample noted. The dimensions could be varied, as necessary or desired, for use with different size grout samples.

In use, the compression pads 26 are inserted in the cavities 34. A retaining cup 24 with the compression pads 26 is placed onto each end 18 of the grout sample 16. This assembly is then placed in the compression testing apparatus 22, see FIG. 3. Particularly, the first planar surface 30 is engagable by one of the test platens 36. The specimen is compressed to failure in a conventional manner.

In accordance with the invention, the steel retaining cups 24 are machined to conform to the planeness of the platens 36 and the cavities 34 provide a means for restricting movement of the compression pads 26 under pressure. The compression pads 26 are adapted to fill any imperfections of the end walls 18 of the sample 16, eliminate formation of air pockets, and prevent possible point pressure which distort the compression test.

Thus, in accordance with the invention, there is described an unbonded capping system for compression testing of grout samples in the form of rectangular prisms.

I claim:

1. An unbonded capping system for compression testing of grout samples in the form of rectangular prisms, comprising:

first and second retaining cups comprising metal blocks each having opposite parallel planar surfaces, a first of the planar surfaces being engagable by a test platen, in use, and a second of the planar surfaces having a rectangular counterbore for receiving one end of the grout sample; and first and second rectangular compression pads each having a hardness in the range of about 50 to 70 durometer, the compression pads being of a size slightly smaller than a size of the rectangular counterbores to be received therein to distribute a test load from the test platens to the grout sample.

2. The unbonded capping system of claim 1 wherein the first and second retaining cups are of high alloy steel construction.

3. The unbonded capping system of claim 1 wherein the first and second retaining cups are cylindrically shaped and the parallel planar surfaces define end walls.

4. The unbonded capping system of claim 1 wherein the first and second rectangular compression pads comprise neoprene pads.

5. The unbonded capping system of claim 1 wherein the rectangular counterbores comprise square counterbores.

6. The unbonded capping system of claim 1 wherein the rectangular counterbore size is larger than a size of an end face of the grout sample.

7. An unbonded capping system for compression testing of grout samples in the form of rectangular prisms, comprising:

first and second retaining cups comprising metal blocks each having opposite parallel planar surfaces, a first of the planar surfaces being engagable by a test platen, in use, and a second of the planar surfaces having a rectangular counterbore for receiving one end of the grout sample; and first and second rectangular elastomeric compression pads, the compression pads being of a size slightly smaller than a size of the rectangular counterbores to be received therein to distribute a test load from the test platens to the grout sample.

8. The unbonded capping system of claim 7 wherein the compression pads each have a hardness in the range of about 50 to 70 durometer.

9. The unbonded capping system of claim 7 wherein the compression pads each have a hardness of about 50 durometer.

10. The unbonded capping system of claim 7 wherein the first and second retaining cups are of high alloy steel construction.

11. The unbonded capping system of claim 7 wherein the first and second retaining cups are cylindrically shaped and the parallel planar surfaces define end walls.

12. The unbonded capping system of claim 7 wherein the first and second rectangular compression pads comprise neoprene pads.

13. The unbonded capping system of claim 7 wherein the rectangular counterbores comprise square counterbores.

14. The unbonded capping system of claim 7 wherein the rectangular counterbore size is larger than a size of an end face of the grout sample.

15. An unbonded capping system for compression testing of grout samples in the form of rectangular prisms, comprising:

first and second retaining cups comprising metal blocks each having opposite parallel planar surfaces, a first of the planar surfaces being engagable by a test platen, in use, and a second of the planar surfaces having a square counterbore for receiving one end of the grout sample; and first and second square elastomeric compression pads each having a hardness in the range of about 50 to 70 durometer, the compression pads being of a size slightly smaller than a size of the square counterbores to be received therein to distribute a test load from the test platens to the grout sample.

16. The unbonded capping system of claim 15 wherein the compression pads each have a hardness of about 50 durometer.

17. The unbonded capping system of claim 15 wherein the first and second retaining cups are of high alloy steel construction.

18. The unbonded capping system of claim 15 wherein the first and second retaining cups are cylindrically shaped and the parallel planar surfaces define end walls.

19. The unbonded capping system of claim 15 wherein the first and second square compression pads comprise neoprene pads.

20. The unbonded capping system of claim 15 wherein the square counterbore size is larger than a size of an end face of the grout sample.

* * * * *